United States Patent [19]
Suda et al.

[11] Patent Number: 5,978,712
[45] Date of Patent: Nov. 2, 1999

[54] STIMULATING APPARATUS FOR PREVENTING URINARY INCONTINENCE

[75] Inventors: Shin Suda; Tadashi Sasaki, both of Tokyo, Japan

[73] Assignee: Nihon Kohden Corporation, Tokyo, Japan

[21] Appl. No.: 08/961,029

[22] Filed: Oct. 30, 1997

[30] Foreign Application Priority Data

Oct. 30, 1996 [JP] Japan .................................. 8-288389

[51] Int. Cl.⁶ ....................................................... A61N 1/08
[52] U.S. Cl. ............................................................ 607/41
[58] Field of Search .................................... 607/2, 40, 41, 607/58, 59, 60, 63, 64, 138, 143

[56] References Cited

U.S. PATENT DOCUMENTS

| | | | |
|---|---|---|---|
| 5,285,781 | 2/1994 | Brodard | 607/59 |
| 5,370,672 | 12/1994 | Fowler et al. | 607/58 |
| 5,653,739 | 8/1997 | Maurer et al. | 607/48 |

FOREIGN PATENT DOCUMENTS

| | | |
|---|---|---|
| WO 97/18857 | 5/1997 | Canada . |
| WO 93/24176 | 12/1993 | United Kingdom . |
| 2278 547 | 12/1994 | United Kingdom . |

Primary Examiner—William E. Kamm
Assistant Examiner—George R. Evanisko
Attorney, Agent, or Firm—Sughrue, Mion, Zinn, Macpeak & Seas, PLLC

[57] ABSTRACT

The stimulating apparatus (1) for preventing urinary incontinence according to the invention includes an event switch (4) for inputting plural sets of urinary incontinence information; a stimulation condition setting unit (5) for setting a condition of stimulation on a living body to an arbitrary value, a stimulation intensity setting unit (3) for adjusting stimulation intensity to an arbitrary level, a central processing unit (6) having an event input judging unit (6d) for judging the plural sets of urinary incontinence information, and a storage unit (6b) for storing the urinary incontinence information, the stimulation conditions, and stimulation history information of a stimulation signal which is output, and a displaying device (7) for displaying the urinary incontinence information, the stimulation conditions, and the stimulation history information.

26 Claims, 3 Drawing Sheets

STIMULATING APPARATUS FOR PREVENTING URINARY INCONTINENCE

BACKGROUND OF THE INVENTION

1. Field of the Invention

The invention relates to a stimulating apparatus for preventing urinary incontinence which applies electrical or magnetic stimulation to a patient suffering from urinary incontinence, and which records the progress of stimulation.

2. Related Art

Generally, it is known that electrical stimulation is effective for prevention or treatment of various kinds of urinary incontinence such as stress incontinence, urge incontinence, and mixed incontinence.

In the prior art, for example, such electrical stimulation is conducted in the following manner. First, surface electrodes are attached to the body surface in the vicinity of the pudendum of the patient; an electrode plug is inserted into the anus, the vagina, or the like; or electrodes are directly embedded into the pelvic floor muscle or the vicinity of the pudendum. Then, electrical stimulation is repeatedly applied at a frequency of several to 100 Hz. This stimulation treatment is continued for one week to several months. The intensity and frequency of electrical stimulation, the stimulation period, the stimulation region, and the like depend on cases and individual differences.

In the treatment with electrical stimulation, specifically, the patient goes to the hospital once each week for several months to be treated with stimulation for 15 to 30 minutes, or, in accordance with instructions of the doctor, the patient is subjected at home two or three times a day to stimulation for about 20 minutes by using a portable electric stimulating apparatus. The patient is provided with a patient diary and instructed to record in detail voiding conditions in daily life, such as the stimulation period, the stimulation intensity, the time of incontinence, the time of voiding, the time of exchange of a diaper or underpants, and the degree of the urge sensation. After a predetermined period elapses, the doctor reads the patient's diary to judge whether the present treatment is effective or not, and decides the subsequent treatment policy.

A test is provided in order to determine the effect of the electrical stimulation treatment. The test may include a urodynamic study (UDS) in which a catheter is inserted into the urethra and the urethral sphincter is pricked with a needle electrode; a test using an ultrasonic diagnostic apparatus; or a pad test in which a stress incontinent patient is given water and then made to take various kinds of bodily exercises at predetermined intervals, and the degree of urinary incontinence is checked. Usually, these tests are used for diagnosis of the type of urinary incontinence, or to check of the presence or absence of voiding disfunction, and hence must be performed by a specialist. Furthermore, inspection apparatuses used in these tests are so expensive that not all hospitals are equipped with such apparatuses.

Regarding the effect of stimulation, the occurrence of urinary incontinence and voiding for each individual is compared with the initial state on the basis of the patient diary, and it is judged whether a change occurred or not. Usually, it is known that, if electrical stimulation is effective, the frequency of urinary incontinence or the like is reduced. However, there are differences among individuals, and hence the judgment cannot be uniformly applied. Practically, therefore, the treatment effect depends on the recording accuracy of the patient diary.

In the treatment of urinary incontinence with electrical stimulation, it is important to know the reason why the treatment is not working, i.e., an effect is not attained although stimulation has been conducted at an appropriate intensity and for a predetermined period, or, even though the patient has conducted stimulation in accordance with instructions of the doctor, an effect is not attained because of insufficient stimulation intensity and stimulation number. In accordance with the result, the subsequent treatment policy is determined.

With respect to a treatment effect, furthermore, the subjective symptom of the patient does not always coincide with the result of the test conducted by the doctor. Even in the case where an unfavorable test result is obtained, when the occurrence of urinary incontinence and voiding are reduced, the patient believes the treatment has worked, with the result that the quality of life (QOL) is improved. Under such circumstances, a patient diary which is used in the prior art is very significant to both the patient and the doctor.

However, aged persons constitute a large portion of urinary incontinent patients, and hence it is difficult to record information in a patient diary, as instructed, for a long term without omission. Furthermore, it is difficult to ask the caregiver to record all items of information because there may arise a problem of privacy.

In the prior art treatment, a UDS test or a pad test is conducted in order to judge the treatment effect. The UDS has a drawback that it has a high degree of invasivenss and inflicts pain on the patient. The pad test is free from invasiveness but compels the patient to take special exercises for predetermined periods. In other words, both the tests are conducted under an unnatural state, and hence cannot obtain a correct state of the symptom.

In the case of an outing or travel, moreover, the patient must always carry the diary together with an electric stimulating apparatus and record information in the diary. This is cumbersome work.

SUMMARY OF THE INVENTION

In view of the problems discussed above, it is an object of the invention to provide a stimulating apparatus for preventing urinary incontinence in which a patient diary is not required, and the stimulation treatment of urinary incontinence and the record of the progress of the treatment can be conducted correctly and easily.

The stimulating apparatus for preventing urinary incontinence of the present invention comprises: inputting means for inputting a plurality of urinary incontinence information; a stimulation condition setting unit for setting a condition of stimulation on a living body to an arbitrary value; a stimulation intensity setting unit for adjusting stimulation intensity to an arbitrary level; judging means for judging the plurality of urinary incontinence information; storing means for storing the urinary incontinence information, the stimulation conditions, and stimulation history information of a stimulation signal which is output; and displaying means for displaying the urinary incontinence information, the stimulation conditions, and the stimulation history information.

The urinary incontinence information is recorded on the basis of the judgement of the kind of urinary incontinence, and the progress of the stimulation treatment, starting from the beginning of stimulation is automatically recorded as the stimulation history information. This information is displayed.

In the present invention, urinary incontinence information before stimulation, and a progress of stimulation and a stimulation effect after stimulation are simultaneously displayed.

Since the urinary incontinence information before and after stimulation, and the stimulation history information are displayed in time sequence on a screen, the progress of stimulation treatment and the treatment effect can be immediately recognized.

DETAILED DESCRIPTION OF THE PREFERRED EMBODIMENTS

Figure 1:
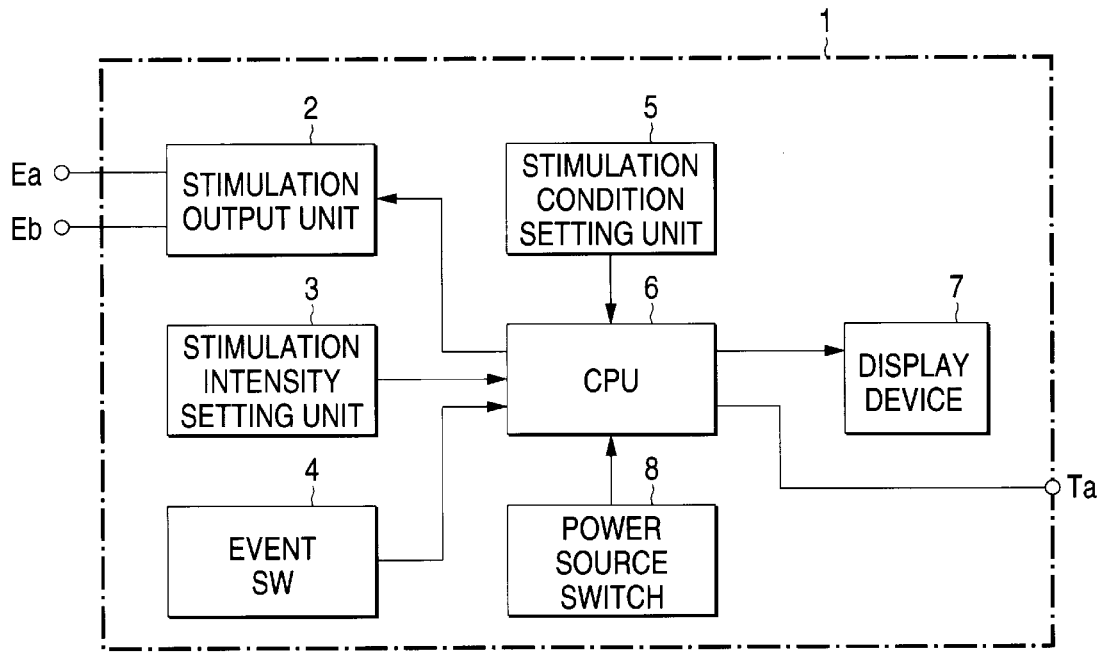
FIG. 1 is a diagram showing the configuration of the stimulating apparatus for preventing urinary incontinence of the invention.
Figure 2:
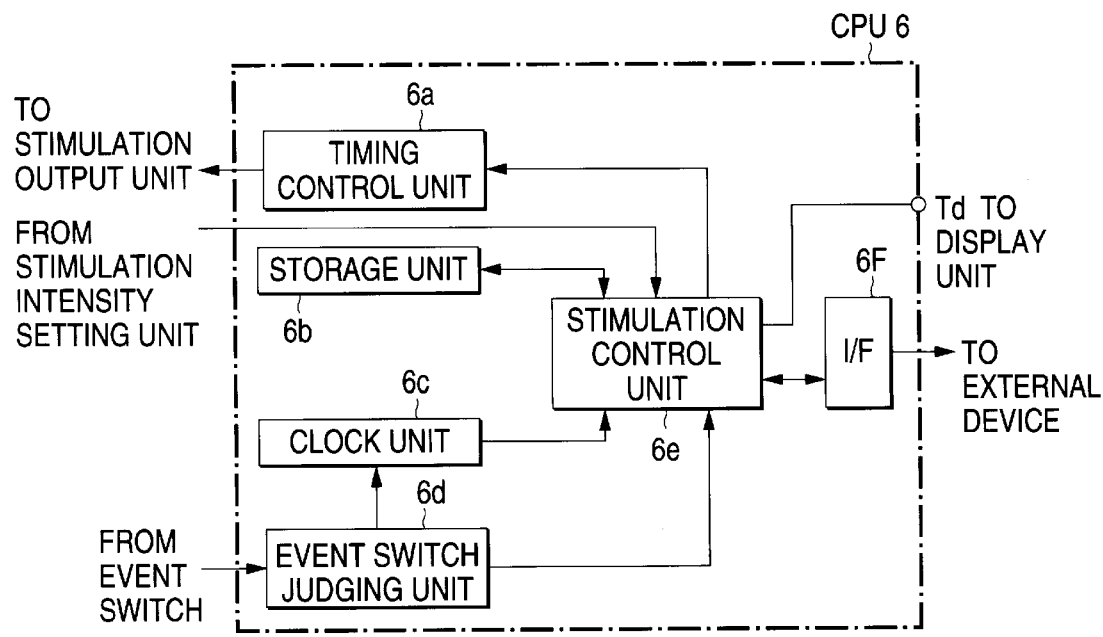
FIG. 2 is a block diagram showing In detail a central processing unit of the embodiment of FIG. 1.

Hereinafter, an embodiment of the stimulating apparatus for preventing urinary incontinence of the invention will be described with reference to the accompanying drawings. FIG. 1 is a block diagram showing the configuration of the embodiment of the invention, FIG. 2 is a block diagram showing in detail functions of a central processing unit, FIG. 3 is a view showing display examples of the embodiment of FIG. 1, and FIG. 30 is a view showing a continuation of FIG. 3.

In FIG. 1, 1 designates the whole of the stimulating apparatus for preventing urinary incontinence of the invention which is configured in the following manner. The reference numeral 2 designates a stimulation output unit to which electrodes Ea and Eb are connected. The electrodes are attached to a predetermined region of the patient, and an electrical stimulation signal is then supplied to the electrodes Ea and Eb. The reference numeral 3 designates a stimulation intensity setting unit which is configured by, for example, a variable resistor, and through which the level of the electrical stimulation signal output from the stimulation output unit 2 can be arbitrarily adjusted by the patient . The number of the electrodes Ea and Eb is not restricted to two and may be adequately increased in accordance with the symptom of the patient.

The reference numeral 4 designates an event switch which consists of, for example, input keys or buttons. The keys or buttons are pressed (1) when urinary incontinence of a large degree occurs, (2) when urinary incontinence of a small degree occurs, (3) when fecal incontinence occurs, (4) when usual voiding is conducted, (5) when the patient feels an urge sensation, (6) when the patient gets up, and (7) when the patient goes to bed, respectively. Denotations such as "large urinary incontinence," "small urinary incontinence," and "fecal incontinence" are formed in the vicinity of the keys or buttons so as to conform to the functions of (1) to (7).

If it is possible to judge whether the degree of urinary incontinence is large or small, an advantage is produced that, even for a patient of a small change in the frequency of urinary incontinence, the treatment effect can be conjectured from the change in the degree of urinary incontinence. Furthermore, from the presence or absence of fecal incontinence, it is possible to judge whether side effects due to electrical stimulation have been produced or not. Particularly in the case when stimulation is conducted in the anus, the rectum is stimulated to be excited, and hence fecal incontinence may occur. Furthermore, it is possible to know whether incontinence, usual voiding, or the like occurred during waking (active) hours or during sleeping hours. Information indicative of a time period when incontinence occurred facilitates the diagnosis on whether the patient suffers from stress incontinence, urge incontinence, or mixed incontinence. Moreover, there is a further advantage that, in the case of mixed incontinence, judgement on which of the symptoms is further improved can be easily done.

The event switch 4 may be configured by a single switch or a plurality of switches. The above-mentioned seven kinds of functions may be realized by changing the settings of the switch. For example, when an event switch for incontinence is pressed two times, it means incontinence of a large degree, and, when the switch is pressed one time, it means incontinence of a small degree. Alternatively, a switch may be allocated for each of the events, or an LCD display screen may be used as a touch panel so that an event is input through the screen.

The reference numeral 5 designates a stimulation condition setting unit which is configured by a key pad having a plurality of input keys, or the like, and through which stimulation conditions such as the stimulation intensity, the stimulation period, and the pulse width of the stimulation signal can be arbitrarily set by the doctor or the health worker in accordance with the state of urinary incontinence of the patient. The disposition of the stimulation condition setting unit S allows the stimulation conditions to be set or changed even when the apparatus is not connected to an external apparatus, whereby the convenience of the apparatus is enhanced.

The reference numeral 6 designates the central processing unit (CPU) which is configured by, for example, a CPU and which controls the whole of the device. The central processing unit 6 comprises a nonvolatile memory as a storage device so as to store history information such as the waveform, period, intensity, and date and time of the stimulation which is actually conducted (hereinafter, such information is referred to as "stimulation history information"), and information such as the kind of the event according to the pressing operation of the event switch 4, and the date and time of the pressing operation (hereinafter, such information is referred to as "event information"). The central processing unit 6 incorporates an interface so as to be connected to an external apparatus via a connecting terminal Ta. According to this configuration, the stimulation conditions and the stimulation history information can be input and output, and the event information can be output, thereby allowing such information to be analyzed in detail. As the external apparatus, useful is an apparatus having a computing function, such as a personal computer, a work station, an electronic organizer, or a mobile computer, or that having a function of printing or displaying information, such as a printer or a large display. Examples of the interface include: communication media through which data can be input to and output from such an external apparatus, such as R5232C, parallel, and IrDA; media such as an FD, and a memory card; and networks such as a telephone line, a modem, and the Internet.

The reference numeral 7 designates a small display device which is configured by a liquid crystal panel or the like. The stimulation conditions, the stimulation history information, and the event information which are output from the central processing unit 6 can be displayed singly or in combination on the display device. Namely, the progress of treatment and the treatment effect can be simultaneously displayed. When information is to be analyzed in detail, the apparatus is connected to a personal computer and hence the detailed analyzation can be conducted while observing the screen of a display device of the computer.

The reference numeral 8 designates a power source switch. When the stimulation 10 intensity setting unit 3 is configured by a variable resistor, the variable resistor may be provided with a switch function so that the stimulation intensity setting unit 3 functions also as the power source switch. In this case, the independent power source switch 8 is not required.

For example, the thus configured stimulating apparatus for preventing urinary 15 incontinence may be housed in a small case, and then carried while being fixed to the waist of the patient with a belt. Alternatively, the apparatus may be put into a pocket of clothes of the patient.

FIG. 2 is a block diagram showing in detail functions of the central processing unit 6. The reference numeral 6a designates a timing control unit which supplies an output signal to the stimulation output unit 2 so as to determine the stimulation frequency, the stimulation waveform, etc.

The reference numeral 6b designates a storage unit which consists of, for example, an EEPROM (Electrically Erasable Programmable ROM) or a battery-backup RAM. The storage unit stores the event information, the stimulation conditions, and the stimulation history information of stimulation which has been actually conducted under the stimulation conditions.

The reference numeral 6c designates a clock unit which is used for knowing the time of occurrence of the event information, and the date and time when the stimulation treatment is conducted.

The reference numeral 6d designates an event input judging unit that judges which one of the keys of the event switch 4 having the above-mentioned three kinds of functions is pressed. The unit then supplies information indicative of the judgement result to a stimulation control unit 6e which will be described below.

The stimulation control unit 6e comprises a memory device such as a battery-backup RAM which stores the stimulation conditions supplied from an external apparatus such as a personal computer via the interface 6f. The stimulation conditions are previously supplied from the external apparatus via the interface 6f and modified in accordance with the cause of urinary incontinence and the symptom severity so as to be set for each patient. The stimulation conditions can be changed also through the stimulation condition setting unit 5 (FIG. 1).

In a stimulation treatment, for a patient whose pain sensation is paralyzed, a burn may be caused by an extremely high intensity of stimulation or by continuously applying stimulation for a long term. In order to prevent such an unfavorable situation from occurring, the stimulation control unit 6e controls the stimulation signal so as to be output with setting limitations of the stimulation intensity and the stimulation period. Furthermore, the setting may be done so that the stimulation intensity is gradually increased. According to this configuration, it is possible to prevent the patient from suffering and pain due to a sudden increase of the stimulation intensity. Data on the limitation of the stimulation signal may be previously programmed as a part of the stimulation conditions into the memory device of the stimulation control unit 6e.

The information to be displayed, such as the event information and the stimulation history information is supplied to the display device 7 shown in FIG. 1, via a terminal Td.

Next, the operation of the configuration of the embodiment shown in FIGS. 1 and 2 will be described. The electrodes Ea and Eb are bonded to a predetermined region of the patient, and the power source switch 8 is then turned on. Stimulation conditions in accordance with the patient are previously set in the stimulation control unit 6e of the central processing unit 6 by using the external apparatus via the interface 6f and then stored. When the stimulation treatment is to be conducted, the timing of the stimulation signal is controlled by the timing control unit 6a and stimulation is conducted on the predetermined region of the patient via the stimulation output unit 2 and the electrodes Ea and Eb.

When the patient feels the intensity of the stimulation signal to be excessive, the patient operates the stimulation intensity setting unit 3 so as to reduce the stimulation intensity. Then, the central processing unit 6 instructs the stimulation output unit 2 to reduce the intensity (for example, the amplitude) of the stimulation signal, and hence the stimulation intensity is reduced.

Next, the patient presses a key of the event switch 4 corresponding to one of the following states: (1) when urinary incontinence of a large degree occurs, (2) when urinary incontinence of a small degree occurs, (3) when fecal incontinence occurs, (4) when usual voiding is conducted, (5) when the patient feels an urge sensation, (6) when the patient gets up, and (7) when the patient goes to bed, respectively. Then, the event input judging unit 6d of the central processing unit 6 judges which of the keys of the event switch is pressed, and sends information indicative of the pressed key to the stimulation control unit 6e. At the same time, information indicative of the date and time of the pressing operation of the event switch is sent from the clock unit 6c to the stimulation control unit 6e. Namely, the operation of pressing any one of the keys of the event switch 4 causes the event information including the date and time of pressing to be input.

The stimulation control unit 6e sequentially supplies, together with the event information from the event switch 4, the stimulation history information such as the stimulation intensity of the stimulation signal output from the stimulation output unit 2 during the stimulation treatment, the stimulation period, and the stimulation waveform to the storage unit 6b so as to be stored therein.

The event information, the stimulation conditions, and the stimulation history information which are stored are sent to the display device 7 and displayed thereon. When the event information and the stimulation history information are combined with each other, a graph indicating, for example, a treatment effect can be displayed. When this graph is observed, it is possible to easily judge whether the treatment effect has been attained or not.

With respect to the event information and the stimulation history information, during an ambulatory care, the apparatus is connected to an external apparatus such as a personal computer via the interface 6f, thereby enabling the doctor to read the correct record and judge the treatment effect on the spot. Therefore, the doctor can decide the subsequent treatment policy.

When the apparatus is connected to a personal computer, furthermore, the event information and the stimulation history information can be transmitted via a telephone line, and at the same time the results can be received. Therefore, a patient at a distant location or a patient who has difficulty in walling can know the treatment effect and the subsequent treatment policy while staying in home.

FIGS. 3 (A) to (D) show a display example of graphs indicating an effect of urinary incontinence which are displayed on the display device of the embodiment. FIG. 3A shows a change in the number of usual voiding per day before and after stimulation (treatment), FIG. 3B shows a change in the number of incontinence per day before and after stimulation, and FIG. 3C shows a change in the number of urge sensation per day before and after stimulation.

Figure 3A:
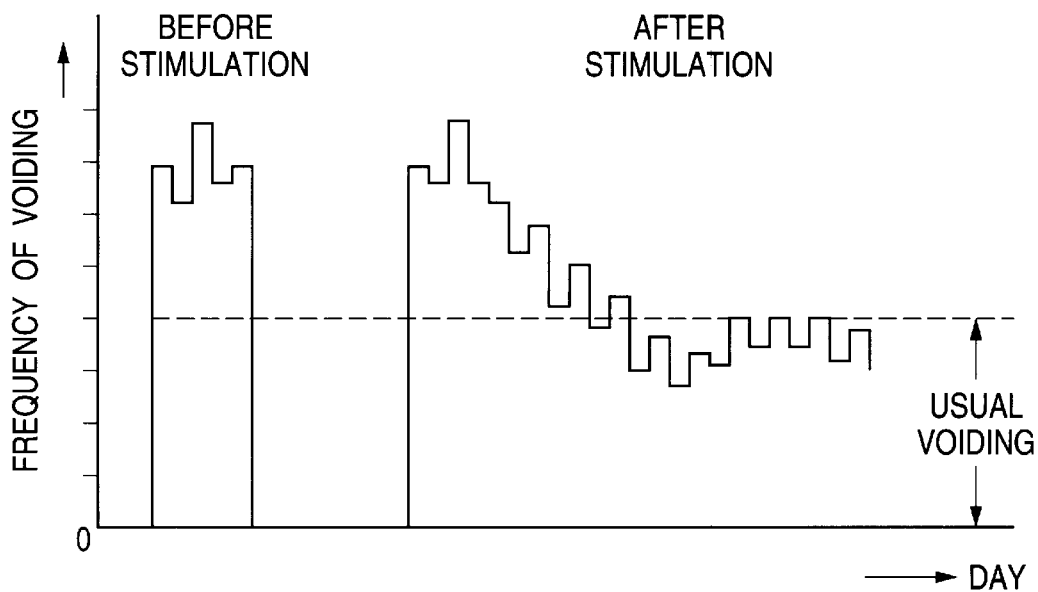
FIGS. 3 (A) through (D) are views showing graphs of display examples of the embodiment of FIG. 1.
Figure 3B:
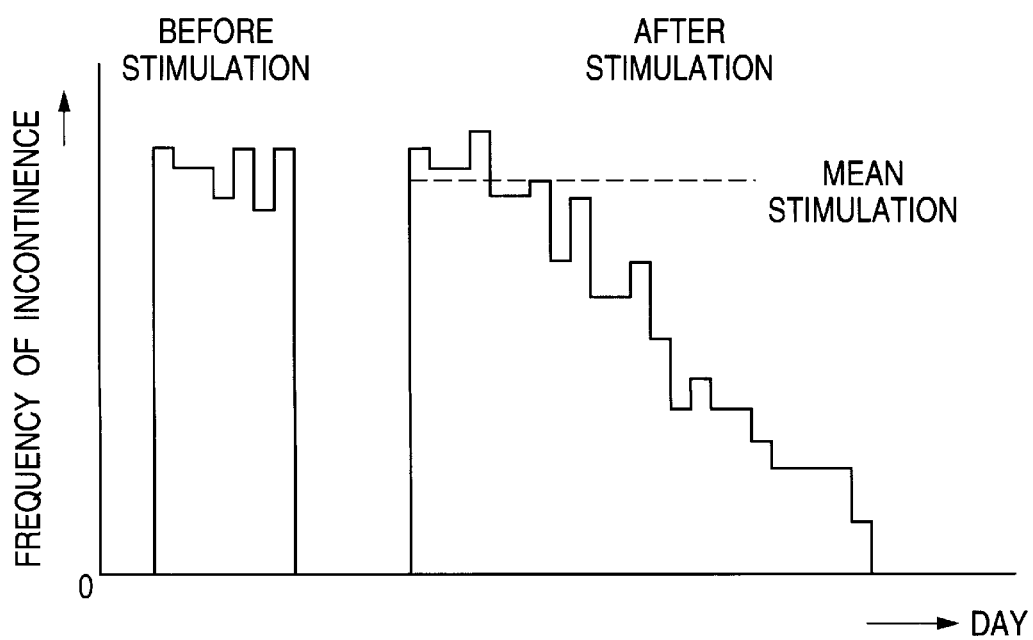
Figure 3C:
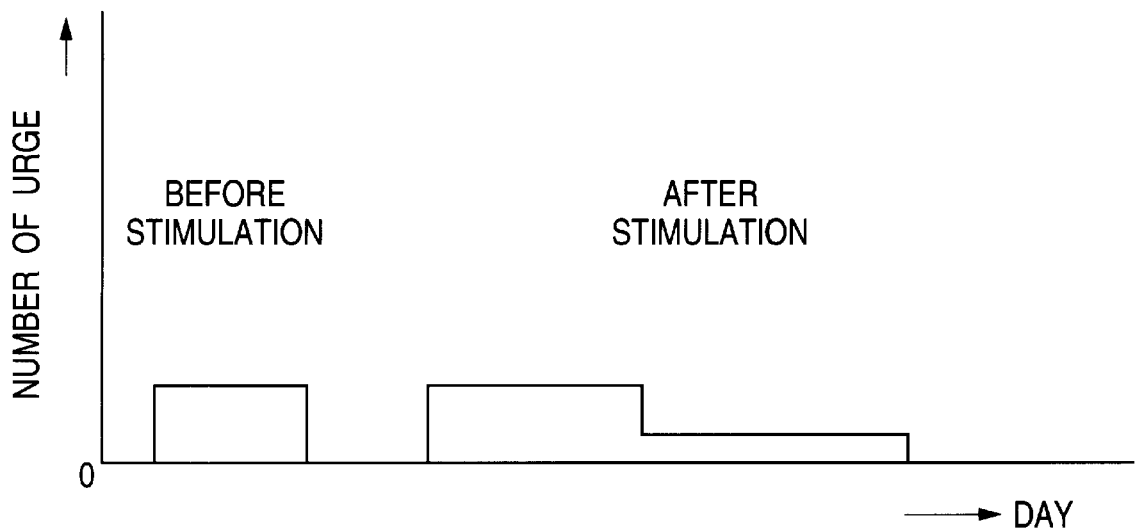
Figure 3D:
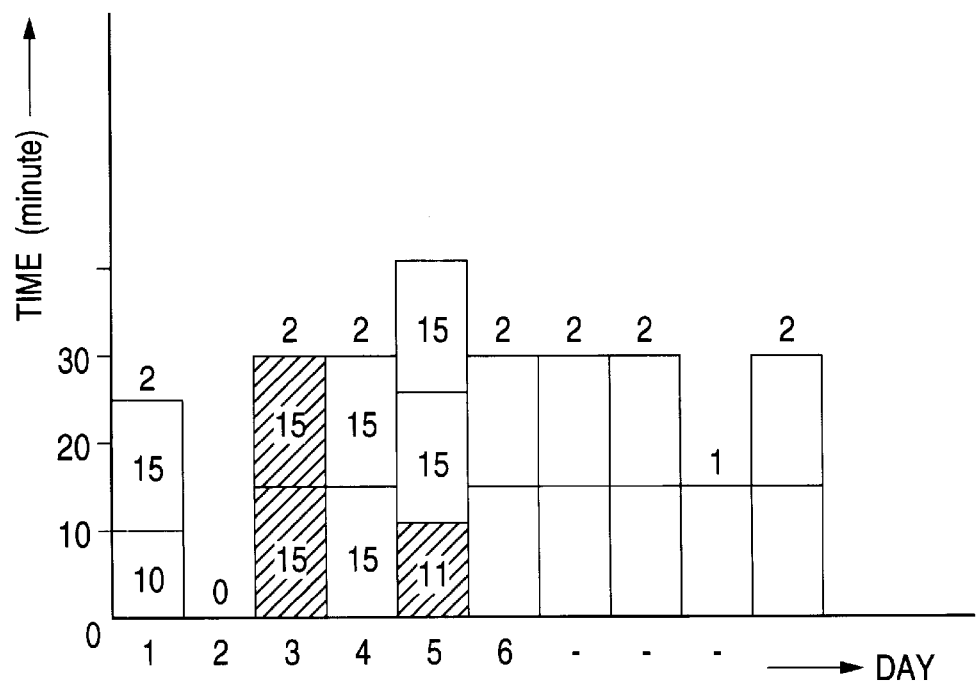

FIG. 3D shows a display example of a graph which indicates the adequateness of the stimulation intensity for each day by using different colors. For example, when stimulation was conducted at a designated stimulation intensity, the stimulation is displayed in blue, and, when stimulation was conducted at a stimulation intensity lower than a designated one, the stimulation is displayed in yellow (in the figure, indicated by diagonal lines). In the figure, the numerals in a bar indicate the stimulation period, and the numeral above a bar indicates the stimulation number. In each bar, the boundary between stimulation treatments is indicated by a thick black line so that they are easily distinguished from each other. As described above, the designated stimulation intensity (maximum permissible stimulation intensity) is set and the intensity can be limited so as not exceed the designated one. Therefore, the adequateness of the stimulation intensity can be sufficiently displayed by using two kinds of displaying states. In this way, the stimulation intensities are displayed in different colors, the stimulation periods are displayed in respective bars, and the stimulation numbers are displayed above respective bars. Therefore, the stimulation state can be judged at a glance.

For example, the graphs of FIGS. 3 (A) to (D) may be used in the following manner. First, the displays of the graphs of FIGS. 3A, 3B, and 3C are observed. As a result of this observation, it is possible to judge the effect of stimulation. If the stimulation is effective, the treatment with the stimulation is continued as it is. If it is judged from the graphs of FIGS. 3A, 313, and 3C that the effect cannot be attained, the graph of FIG. 3D is displayed. From this graph, it is possible to judge whether the stimulation has been conducted at the instructed intensity, period, and number or not.

For example, the treatment effect may be judged in the following manner. The 25 degree of the treatment effect can be evaluated While defining two indices, i.e., improvement of frequency of voiding, and that of the frequency of urinary incontinence as follows:

$$\text{Improvement of the frequency of voiding} = 1 - \frac{A - C}{B - C}$$

where
- A: average of the frequency of voiding per day for one week after the start of the 5 treatment,
- B: average of the frequency of voiding per day before the treatment, and
- C: normal frequency of voiding per day.

In the above, C is determined by the doctor in accordance with the attributes (sex, age, etc.) of the patient.

$$\text{Improvement of the frequency of urinary incontinence} = 1 - \frac{D}{E}$$

where
- D: average of the frequency of urinary incontinence per day after the start of the treatment, and
- E: average of the frequency of urinary incontinence per day before the treatment. The two improvements can be displayed as indices of the treatment effect.

Also when the frequency of voiding is reduced into a predetermined range in the vicinity of the normal frequency of voiding, or when the number of incontinence is reduced to a value smaller than a predetermined one, it is possible to judge that the treatment effect has been attained. The doctor can synthetically evaluate the treatment effect from these data and the degree of recovery which the patient feels.

The judgement on the treatment effect may be calculated by the CPU incorporated in the main unit of the urinary incontinence treatment stimulation device. Alternatively, the judgment may be calculated by a CPU of an external apparatus connected to the main unit via the interface. When the external apparatus stores past data relating to the treatment of urinary incontinence or those relating to medication for the treatment of urinary incontinence, the treatment effect for a long term can be synthetically evaluated and obtained. The treatment effect and the like may be displayed on the display device disposed in the urinary incontinence treatment stimulation device, or on the external apparatus.

In the embodiment described above, the apparatus operates on the basis of electrical 5 stimulation. Even an apparatus based on, for example, magnetic stimulation can be similarly configured and attain the same effects.

As described above, according to the stimulating apparatus for preventing urinary incontinence of the present invention, event information and stimulation history information which are more accurate than those of the prior art which are based on the recording in a patient diary can be obtained correctly and rapidly.

Since a patient diary is not required, the patient is liberated from cumbersome works such as the work of recording information in detail.

Via an interface such as a network, furthermore, event information and stimulation history information can be sent to the system of the hospital such as a personal computer or a work station, adequate stimulation conditions corresponding to the progress of the treatment can be input to the stimulation device, and results of a diagnosis by the doctor can be received. For a patient at home which is remote from the hospital or a patient who has difficulty in walking, therefore, the device is remarkably higher in convenience than a patient diary used in the prior art.

According to the present invention, since the progress of treatment and the treatment effect can be displayed in time sequence, the apparatus has advantages that the symptom can be very easily judged, and that the treatment policy can be rapidly judged.

What is claimed is:

1. A urinary incontinence treatment stimulation device comprising:
   inputting means for inputting urinary incontinence information;
   a stimulation condition setting unit for setting a stimulation charactenstic for a patient to a set value;
   a stimulation intensity setting unit for adjusting a stimulation intensity of said stimulation characteristic;
   stimulation means for outputting a stimulation signal in accordance with said stimulation characteristic and said stimulation intensity;
   storing means for storing information including said urinary incontinence information, said stimulation characteristic, and stimulation history information of said stimulation signal; and
   control means, connected to said stimulation condition setting unit, said stimulation intensity setting unit and said storing means, for controlling said stimulation means in response to said stimulation characteristic and said stimulation intensity.

2. The urinary incontinence treatment stimulation device according to claim 1, further comprising:

processing means for determining a treatment effect level on the basis of said urinary incontinence information.

3. The urinary incontinence treatment stimulation device according to claim 2, further comprising:

display means for displaying said treatment effect level.

4. The urinary incontinence treatment stimulation device according to claim 1, further comprising:

display means for displaying at least one of said urinary incontinence information and said stimulation history information.

5. The urinary incontinence treatment stimulation device according to claim 4, wherein said control means judges whether said stimulation intensity is equal to a predetermined stimulation intensity; and wherein said display means is arranged to display, in the display of said stimulation history information, a result of a judgment by said control means.

6. A urinary incontinence treatment stimulation apparatus, comprising:

a urinary incontinence treatment stimulation device comprising:

inputting means for inputting urinary incontinence information;

a stimulation unit for stimulating a patient;

a stimulation intensity setting unit for adjusting a stimulation intensity of said stimulation unit;

storing means for storing said urinary incontinence information, and stimulation history information of said stimulation intensity signal; and control means, connected to said stimulation intensity setting unit and said storing means, for controlling said stimulation unit in response to said incontinence information and said stimulation intensity; and an external apparatus for connection to said urinary incontinence treatment stimulation apparatus.

7. The urinary incontinence treatment stimulation apparatus according to claim 6, further comprising:

an interface through which signals are transmitted between said urinary incontinence treatment stimulation device and said external apparatus;

wherein said external apparatus comprises:

receiving means for receiving said urinary incontinence information and said stimulation history information stored in said storing means; and display means for displaying at least one of said urinary incontinence information and said stimulation history information.

8. The urinary incontinence treatment stimulation apparatus according to claim 7, wherein said external apparatus comprises a stimulation condition setting unit for setting a condition of stimulation, which is to by applied to a patient by said stimulation unit, to a predetermined value.

9. The urinary incontinence treatment stimulation apparatus according to claim 7, further comprising:

processing means for determining said treatment effect level on the basis of said urinary incontinence information.

10. The urinary incontinence treatment stimulation apparatus according to claim 9, further comprising:

display means for displaying said treatment effect level.

11. The urinary incontinence treatment stimulation apparatus according to claim 9, wherein said control means judges whether said stimulation intensity is equal to a predetermined stirnulation intensity and wherein said display means is arranged to display, in the display of said stimulation history information, a result of a judgment by said control means.

12. A method for treating urinary incontinence, comprising:

setting, on a urinary incontinence treatment stimulation device, a stimulation characteristic for a patient to a set value;

adjusting a stimulation intensity of said stimulation characteristic;

outputting a stimulation signal in accordance with said stimulation characteristic and said stimulation intensity;

inputting urinary incontinence information into said urinary incontinence treatment device in response to said stimulation signal; and storing information including said urinary incontinence information, said stimulation characteristic, and stimulation history information based on said stimulation signal.

13. The method according to claim 12, further comprising:

determining a treatment effect level on the basis of said urinary incontinence information.

14. The method according to claim 13, further comprising the step of:

displaying said treatment effect level.

15. The method according to claim 12, further comprising:

displaying at least one of said urinary incontinence information and said stimulation history information.

16. The method according to claim 15, wherein said displaying step comprises:

judging whether said stimulation intensity is equal to a predetermined stimulation intensity;

displaying a result of said judging step.

17. A method for treating urinary incontinence, comprising:

setting, on a urinary incontinence treatment stimulation device, a stimulation characteristic for a patient to a set value;

adjusting a stimulation intensity of said stimulation characteristic;

outputting a stimulation signal in accordance with said stimalation characteristic and said stimulation intensity;

inputting urinary incontinence information into said urinary incontinence treatment stimulation device;

storing information including said urinary incontinence information, said stimulation characteristic and stimulation history information based on said stimulation signal as stored information; and transmitting said information to an external apparatus.

18. The method according to claim 17, further comprising:

receiving, at said external apparatus, said stored information;

displaying, on said extemal apparatus, at least one of said urinary incontinence information and said stimulation history information.

19. The method according to claim 18, further comprising:

setting a condition of stimulation, from said extenal apparatus, to be applied to a patient to a predetermined value.

20. The method according to claim 18, further comprising:
  determining a treatment effect level on the basis of said urinary incontinence information.

21. The method according to claim 20, further comprising the step of:
  displaying said treatment effect level.

22. The method according to claim 18, wherein said displaying step comprises:
  determining whether said stimulation intensity is equal to a predetermined stimulation intensity displaying a result of said determining step.

23. An incontinence treatment stimulation device comprising:
  stimulation condition setting means for setting a stimulation condition including at least one of stimulation characteristic and stimulation intensity;
  stimulation means for outputting a stimulation signal in accordance with said stimulation condition from said stimulation condition setting means;
  inputting means for inputting incontinence information including at least one of occurrence of incontinence, conduction of usual voiding, feeling of an urge sensation, awake time and sleep time;
  clock unit for providing time of activation of said inputting means; and
  storing means for storing at least said incontinence information, said stimulation condition, first time information output from said clock unit indicative of the time when said inputting means is operated, and second time information output from said clock unit indicative of the time when the stimulation in accordance with said stimulation condition is conducted.

24. An incontinence treatment stimulation apparatus comprising:
  stimulation control means for controlling stimulation intensity by setting a predetermined stimulation intensity;
  stimulation intensity adjusting means for adjusting said predetermined stimulation intensity;
  stimulation means for outputting a stimulation signal having one of said predetermined stimulation intensity and an adjusted stimulation intensity when said predetermined stimulation intensity is adjusted by operation of said stimulation intensity adjusting means;
  a clock unit for providing time information;
  storing means for storing at least said predetermined stimulation intensity set by said stimulation control means, adjusted stimulation intensity and time information output from said clock unit indicative of time stimulation is conducted as stimulation history information judging means for determining whether said stimulation intensity is equal to said predetermined stimulation intensity; and
  display means for displaying said stimulation history information and an output from said judging means.

25. The incontinence treatment stimulation apparatus according to claim 24, further comprising:
  inputting means for inputting incontinence information including at least one of occurrence of incontinence, conduction of usual voiding, feeling of an urge sensation, awake time and sleep time;
  wherein said storing leans further stores said incontinence information and time information output by said clock unit indicative of the time when said inputting means is operated.

26. A method for treating incontinence, comprising:
  setting a predetermined stimulation intensity on a urinary incontinence treatment stimulation device;
  storing said predetermined stimulation intensity;
  adjusting said stimulation intensity of said urinary incontinence treatment stimulation device by a patient when needed;
  storing an adjusted stimulation intensity when said stimulation intensity is adjusted;
  outputting a stimulation signal in accordance with said stimulation intensity;
  storing said stimulation signal as incontinence history information;
  inputting urinary incontinence information into said urinary incontinence treatment stimulation device by the patient when the patient experiences incontinence states;
  judging whether said stimulation intensity is equal to said predetermined stimulation intensity; and
  evaluating the effectiveness of treatment based on a result of said judging step.

* * * * *